United States Patent [19]

Ho

[11] Patent Number: 4,857,452
[45] Date of Patent: Aug. 15, 1989

[54] ASSAY FOR CARCINOMA OF BREAST, COLON AND OVARY

[75] Inventor: May-Kin Ho, Carlisle, Mass.

[73] Assignee: E. I. Du Pont de Nemours and Company, Wilmington, Del.

[21] Appl. No.: 937,771

[22] Filed: Dec. 4, 1986

[51] Int. Cl.$^4$ .................. G01N 33/53; G01N 33/577
[52] U.S. Cl. ................................ 435/7; 435/172.2; 435/240.27; 436/548; 436/813; 935/110
[58] Field of Search ................ 435/172.2, 240.27, 7; 935/110; 436/813, 548

[56] References Cited

U.S. PATENT DOCUMENTS

| 4,579,827 | 4/1986 | Sakamoto | 436/536 |
| 4,612,282 | 9/1986 | Schlom | 435/68 |

FOREIGN PATENT DOCUMENTS

| 160446 | 6/1985 | European Pat. Off. |
| 0154550 | 9/1985 | European Pat. Off. |
| 171083 | 12/1986 | European Pat. Off. |
| WO85/02411 | 6/1985 | PCT Int'l Appl. |

OTHER PUBLICATIONS

Ho et al., Fed. Proc., 45, 984, Mar. 5, 1986.
Ceriani et al., Proc. Nat'l. Acad. Sci., 79, 5420–5424 (1982).
Goodall et al., Br. J. Cancer, 52, 177–182 (1985).
Hayes et al., J. Clin. Invest, 75, 1671–1678 (1985).
Hilkens et al., Cancer Research, 46, 2582–2587 (May 1986).
Herlyn et al., J. Clin. Immunology, 2, 135–140.
Haglund et al., Br. J. Cancer, 53, 197–202 (1986).
Klug et al., Cancer Research, 44, 1048–1053 (1984).
Metzer et al., Cancer Research, 42, 601–608 (1982).
Paisa et al., Cancer Letters, 17, 217–222 (1982).
Moll et al., Cell. vol. 31, pp. 11–24, Nov. 1982.
Ho et al., Cancer Research, vol. 47, pp. 241–250, Jan. 1, 1987.
Gail, M. H. 1979, Some Statistical Methods for Evaluating Immunodiagnostic Tests, In: Heberman et al., eds., Immunodiagnosis of Cancer, Part I, New York: Marcel Dekker, pp. 20–37.

Primary Examiner—Christine M. Nucker
Assistant Examiner—D. John Griffith, Jr.

[57] ABSTRACT

Colorectal, breast or ovarian cancer can be detected by means of a blood, plasma, serum, urine or feces assay for elevated levels of 47D10 antigen using a monoclonal antibody to the antigen.

3 Claims, No Drawings

ASSAY FOR CARCINOMA OF BREAST, COLON AND OVARY

FIELD

This invention relates to non-invasive detection or monitoring of breast, colorectal and ovarian cancer. More specifically, it relates to immunoassay of blood, plasma, serum, urine or feces for antigen recognized by murine monoclonal antibody (MAb) 47D10.

BACKGROUND

EPO published application 85301540.2, publication number 154,550, discloses MAb 47D10 and fragments thereof, and diagnostic and therapeutic processes employing the antibody or fragments. The antibody was produced by the hybridoma technique of Kohler and Milstein, using A549 lung adenocarcinoma cells as immunogen and for ELISA screening of hybridoma supernatants. The hybridoma designated 47D10 was selected with significantly greater reactivity for the immunogen A549 than normal embryonic lung fibroblast cells. Hybridoma 47D10 is on deposit in the American Type Culture Collection with accession number HB8504, under the terms of the Budapest Treaty.

The above EPO application reports results of ELISA tests of 47D10 hybridoma supernatant for reactivity with various fixed normal and tumor cell lines as well as results of ELISA tests of purified 47D10 MAb with live cells of the same normal and tumor lines. The results showed significant antibody binding to the immunogen A549 and a colon adenocarcinoma cell line, but only slight reactivity with breast carcinoma and melanoma lines.

The EPO application also reports results of immunohistochemical studies of 47D10 MAb on a variety of normal and neoplastic tissues. The antibody reacted with 38 of 40 pancreatic adenocarcinomas, 5 of 8 lung adenocarcinomas, 8 of 11 colon adenocarcinomas and 4 of 7 breast infiltrating ductal carcinomas. However, a colon adenocarcinoma metastatic to liver and a breast adenocarcinoma did not react with the antibody. Normal tissues, pancreas tissue with pancreatitis, breast tissue with fibrocystic disease and ovarian cystadenomas did not react. Metastatic pancreatic tumor cells were detected in lymph nodes by the antibody.

It is stated in the EPO application that 47D10 MAb is useful in the diagnosis of primary and metastatic pancreatic tumor cells by conventional in vivo diagnostic methods and also by conventional in vitro diagnostic procedures such as the assay of human blood samples or other body fluids.

Ho et al., Fed. Proc. 45, 984 (1986) reports that the 47D10 tumor-associated antigen is a group of surface glycoproteins of 63-97 Kd (average 85 Kd) molecular weight. However, it is now known that the antigen is a group of surface glyco proteins ranging in molecular weight from 67 Kd to 98 Kd. EPO publication 154,550 and the Ho et al. article are incorporated herein by reference.

Serum and plasma assays to detect other tumor-associated antigens have been reported. Ceriani et al., Proc. Nat'l. Acad. Sci., 79, 5420-5424 (1982) reports the presence of high levels of 150 Kd, 70 Kd and 46 Kd human mammary epithelial antigens in sera of breast cancer patients and a monoclonal antibody Mc 3 to the 46 Kd antigen raised against human milkfat globule membrane. PCT Publication Number WO 85/02411 reports a monoclonal antibody 3 El-2 raised against ductal breast carcinoma cells which detects an antigen present in elevated levels in the serum of patients with carcinoma of the breast. EPO Publication Number 160446 reports a 330 Kd antigen which is shed by breast cancer cells, monoclonal antibodies 21DD5 and 21DD7 to the antigen raised against breast carcinoma cells, and use of the monoclonals in a plasma assay to detect breast cancer. Goodall et al., Br. J. Cancer, 52, 177-182 (1985) reports work to establish an assay for detection of Ca antigen in sera of breast cancer patients, states that presence of Ca antigen in serum had no diagnostic significance, but indicates that assay of sequential serum samples could be of prognostic value since sera of half of patients with metastatic spread had elevated levels of the antigen. Hayes et al., J. Clin. Invest, 75, 1671-1678 (1985) reports a mouse monoclonal antibody DF3 prepared against a membrane-enriched fraction of a human breast carcinoma which reacts with a 300 Kd mammary epithelial antigen, and use of the antibody for detection the antigen in plasma of breast cancer patients. Hilkeus et al., Cancer Research, 46, 2582-2587 (May, 1986) reports use of monoclonal antibody 115D8, raised against human milkfat globule membranes, in a radioimmunoassay to detect elevated levels of MAM-6, a >400 Kd epithelial membrane antigen, in sera of breast cancer patients.

Herlyn et al. J. Clin. Immunology, 2, 135-140 reports monoclonal antibodies 19-9, 52a and $C_414$ raised against colon carcinoma cell lines and their use in a serum assay to detect colorectal, gastric and pancreatic carcinoma. The antigen detected by two of these antibodies is reported to be a monosialoganglioside. Haglund et al., Br. J. Cancer, 53, 197-202 (1986) also reports evaluation of antibody 19-9 in a serum assay for pancreatic cancer. EPO publication Number 171,083 discloses monoclonal antibodies KMO1 and KMO2 raised against a 700-1,500 Kd fraction of a colon cancer cell line, and their use in a serum assay to detect pancreas, colon and liver cancer.

Klug et al. Cancer Research, 44, 1048-1053 (1984) reports use of a murine monoclonal antibody OC125 in an immunoradiometric serum assay for an ovarian carcinoma associated antigen CA125.

SUMMARY OF THE INVENTION

It has now been discovered that the presence in a patient of breast, colorectal or ovarian cancer can be detected by assaying blood, plasma, serum, urine or feces of the patient for presence of 47D10 antigen using a monoclonal antibody to the antigen such as MAb 47D10 or an immunoreactive fragment of such an antibody. The assay is especially useful in detecting and monitoring breast cancer, most especially in patients with more than two metastatic sites, and in detecting and monitoring colorectal cancer in patients with liver metatases.

These are unexpected findings for several reasons. MAb 47D10 was raised against a lung carcinoma line, whereas the MAb's reported in the above-cited references to be useful in serum assays for breast, colorectal or ovarian cancers were raised against breast, colorectal and ovarian cell lines, respectively. MAb 47D10 in immunohistochemical studies stained lung cells strongly but breast cells weakly; yet in serological studies reported below, only low levels of 47D10 antigen were found in sera of lung cancer patients versus high levels in sera of breast cancer patients. In the immunohistochemical studies MAb 47D10 stained 4 of 7 infiltrating ductal breast carcinomas but failed to stain breast fibrodenoma or adenocarcinoma lines. In the immunohistochemical studies, 47D10 MAb differentiated between pancreatic cancer and benign pancreatitis, but in serological studies it did not. In the immunohistochemical studies 47D10 MAb failed to stain a colon adenocarcinoma metastatic to liver, but in the serological studies high levels of 47D10 antigen were detected in sera of patients with colorectal cancer metastatic to liver. In the immunohistochemical studies 47D10 MAb failed to stain ovarian cystadenoma cells, but significant levels of 47D10 antigen were detected in sera of ovarian cancer patients.

MAb 47D10 is an IgG, kappa molecule. Digestion with proteolytic enzymes such as pepsin produces immunoreactive F(ab')$_2$ fragments which can also be used in the assay of this invention.

DETAILED DESCRIPTION

A human tumor cell line which expresses high amounts of the 47D10 antigen, is grown to confluency in tissue culture bottles. The cells are collected by scraping the insides of the bottles with a rubber policeman. The cells are then washed three times with phosphate-buffered saline pH 7.3 (PBS), resuspended in PBS with 10 U/ml of deoxyribonuclease I and 1 mM phenyl methyl sulfonyl fluoride (PMSF), and disrupted by nitrogen cavitation. The cell suspension is layered onto approximately an equal volume of 41% sucrose solution in a centrifuge tube and ultracentrifuged at 100,000×g for 60 min. The cell fraction concentrated in the interface of the PBS and sucrose solution is enriched for cell membrnnes contaning the 47D10 antigen. This fraction is collected and washed three times in PBS with 1 mM PMSF and stored in PBS at −70° C. until use.

To determine the level of 47D10 antigen in a serum sample, a competition enzyme-linked immunoassay (ELISA) is used. This assay involves two phases. The first is the preincubation phase where the serum is serially diluted and reacted with a limiting amount of the 47D10 monoclonal antibody (MAb). Both the serum and MAb are diluted in PBS with 1% w/v bovine serum albumin (BSA). Typically, 30 μl of diluted serum are incubated with 30 μl of 47D10 MAb (60 ng/ml) in a microtiter plate for two hours at room temperature. This allows serum antigens to bind to the 47D10 MAb. Then 50 μl of the mixture of serum and MAb are transferred to a second microtiter plate which has been coated with 350 ng/well of tumor cell membranes (prepared as described above). After an incubation of one hour at 37° C., the wells are washed three times with PBS with 0.1% BSA and one time with PBS. To detect the bound 47D10 MAb, 50 μl of goat anti-mouse IgG antibody conjugated to horseradish peroxidase (GAMHRP), diluted 1:15,000 in PBS-1% BSA, are added to each well. The plate is incubated for 60 min. at 37° C., washed three times with PBS-0.1% BSA and then two times with PBS. The presence of GAMHRP is determined by adding 50 μl of the substrate of HRP, 0.2% w/v o-phenylenediamine (OPD) in a buffer of 0.009M citric acid, 0.03M $K_2HPO_4$ containing 0.15% hydrogen peroxide. HRP in combination with its substrate results in a yellow colored product, development of which occurs in approximately 10 min. at 37° C. The enzymatic reaction is terminated by the addition of 50 μl of 4.5M $H_2SO_4$. The resultant enzyme reaction product is quantitated spectrophotometrically at 488 nm. During this second phase of the assay, any unbound 47D10 MAb from the first phase will bind to the membrane-coated plate. The maximal binding on each plate is determined by including 2–4 wells with 30 μl of 47D10 MAb (60 ng/ml) which are preincubated with PBS-1% BSA, instead of serum, during the first phase of the assay. By using several serial dilutions of each serum sample, the titer (inverse of dilution) required to give 50% of the maximal binding can be defined. This half-maximal titer (HMT) is directly correlated to the amount of 47D10 antigen present in a given sample.

A panel of 264 serum samples from the National Cancer Institute Diagnostic Serum Bank was examined using the above assay. Results are shown in Tables I–III below:

TABLE I

Comparison of Marker Values by Diagnostic Group

| Diagnostic Group | N | Median Titer | Wilcoxon p-value[1] |
|---|---|---|---|
| Lung Cancer | 30 | 10.0 | 0.035 |
| Normal | 50 | 10.0 | |
| Colorectal Cancer | 30 | 10.0 | 0.0008 |
| Normal | 50 | 10.0 | |
| Breast Cancer | 30 | 12.0 | <0.0000 |
| Benign Breast | 29 | 10.0 | |
| Breast Cancer | 30 | 12.0 | 0.0001 |
| Normal Females | 32 | 10.0 | |
| Pancreas Cancer | 30 | 16.6 | 0.100 |
| Benign Pancreas | 13 | 10.7 | |
| Pancreas Cancer | 30 | 16.6 | <0.0000 |
| Normal | 50 | 10.0 | |
| Ovarian Cancer | 24 | 10.2 | 0.010 |
| Normal Females | 32 | 10.0 | |
| Melanoma | 28 | 10.0 | 0.78 |
| Normal | 50 | 10.0 | |

[1]Gail, M. H. 1979. Some statistical methods for evaluating immunodiagnostic tests. In: Heberman, R., McIntire, R., eds. Immunodiagnosis of Cancer. Part I. New York: Marcel Dekker. pp. 20–37.

TABLE II

| | % Sensitivity | % Specificity | Cut-Off |
|---|---|---|---|
| Lung Ca vs. Normal | 40 | 84 | 10.0 |
| Colorectal Ca vs. Normal | 40 | 94 | 12.9 |
| Breast Ca vs. Normal | 60 | 88 | 11.0 |
| Pancreatic Ca vs. Normal | 63 | 98 | 14.1 |
| Ovarian Ca vs. Normal | 50 | 84 | 10.2 |
| Breast Ca vs. Benign Breast | 63 | 93 | 10.0 |
| Pancreatic Ca vs. Benign Pancreas | 100 | 0 | 10.0 |

TABLE III

Ancillary Analysis

| Comparison Group | N | Median Titer | Wilcoxon p-value |
|---|---|---|---|
| Metastases to Liver-Colon Ca | 12 | 21.9 | <0.0000 |
| No Liver Involvement-Colon Ca | 18 | 10.0 | |
| >2 Metastatic Sites-Breast Ca | 8 | 13.5 | 0.029 |
| ≦2 Metastatic Sites-Breast Ca | 22 | 10.5 | |

Summarizing the above results, significant increase in 47D10 antigen levels was found in all cancer groups except melanoma when compared with normal controls (p<0.05) (Table I). The assay failed to distinguish pancreatic cancer from benign pancreatic disease. There was a substantial difference betwen 47D10 antigen levels in colorectal cancer paitnets with metastases to liver versus those with metastases to other organs. In breast cancers, substantially increased 47D10 antigen levels were detected in patients with more than two versus those with two or less metastatic sites. Despite strong immunohistochemical staining of lung carcinoma by the 47D10 MAb, only low levels of 47D10 antigens were found in sera of patients with lung cancer.

Modifications of the above competition ELISA can be used. For example, GAMHRP can be substituted by radiolabeled goat anti-mouse Ig antibody if a radioimmunoassay is desired. In addition, 47D10 MAb labeled directly with an enzyme, fluorescent tag, radioisotope, or biotin can be used during the second phase of the assay. This will eliminate the need of a second step detector antibody such a GAMHRP.

A sandwich assay can also be developed. This involves the conjugation or adsorption of the 47D10 MAb or a substance which is reactive with the 47D10 antigen, such as a lecithin, to a solid support. Examples of solid supports are wells of a microtiter plate, polystyrene beads, or magnetic beads. The MAb or lectin on the solid support can be used to "capture" serum antigens which are subsequently detected by labeled 47D10 MAb.

I claim:

1. A method of assisting in th diagnosis of or monitoring breast, colorectal or ovarian cancer which comprises assaying the blood, plasma, serum, urine or feces of a person suspected of having or known to have breast, colorectal or ovarian cancer by reacting monoclonal antibody 47D10 or an immunoreactive fragment thereof with the blood, plasma, serum, urine or feces and determining whether antibody binding has occurred.

2. Method of claim 1 wherein the serum is assayed and the cancer is breast cancer.

3. Method of claim 1 wherein the serum is assayed and the cancer is colorectal cancer metastatic to liver.

* * * * *